United States Patent [19]

Vanassche et al.

[11] 4,026,708

[45] May 31, 1977

[54] DIRECT-POSITIVE SILVER HALIDE EMULSIONS HAVING INCORPORATED DEVELOPERS

[75] Inventors: Willy Joseph Vanassche, Kontich; Robert Joseph Pollet, Vremde; Jozef Frans Willems, Wilrijk; Antoon Leon Vandenberghe, Hove; Jules Robert Berendsen, Deurne; Herman Alberik Pattyn, Kapellen, all of Belgium

[73] Assignee: AGFA-GEVAERT, N.V., Mortsel, Belgium

[22] Filed: Feb. 21, 1975

[21] Appl. No.: 552,036

[30] Foreign Application Priority Data

Feb. 28, 1974 United Kingdom ............. 9105/74

[52] U.S. Cl. .................................. 96/95; 96/64
[51] Int. Cl.² .................... G03C 1/06; G03C 5/24
[58] Field of Search .............................. 96/64, 95

[56] References Cited

UNITED STATES PATENTS

| 3,519,428 | 7/1970 | Ishikawa et al. | 96/95 |
| 3,632,340 | 1/1972 | Illingsworth | 96/64 |
| 3,650,749 | 3/1972 | Willems et al. | 96/95 |

*Primary Examiner*—Mary F. Kelley
*Attorney, Agent, or Firm*—A. W. Breiner

[57] ABSTRACT

Direct-positive emulsions are described comprising incorporated developing agents wherein the developing agents are 1,4-dihydroxybenzene compounds of which at least one of the hydroxyl groups has been esterified to form a hydrolyzable aliphatic acyloxy group comprising a quaternary ammonium group.

8 Claims, No Drawings

DIRECT-POSITIVE SILVER HALIDE EMULSIONS HAVING INCORPORATED DEVELOPERS

The present invention relates to direct-positive silver halide emulsions having incorporated developing agents.

It is known that direct-positive images can be obtained with certain types of photographic silver halide emulsions without previously forming a negative image. For example, the silver halide grains can be fogged during or after coating on a support by an overall exposure to actinic radiation or by overall chemically fogging e.g. by means of reducing agents. Upon image-wise exposure of the prefogged emulsions the development centers formed by said fogging are destroyed at the exposed areas and remain at the unexposed areas. By development of the emulsion after image-wise exposure a direct-positive image is formed.

Contrary to negative image formation where developable silver specks are formed by image-wise exposure in the exposed areas, which can be represented schematically as follows:

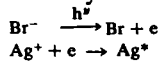

($e$ = photoelectron, $Ag^*$ = developable speck) direct-positive image formation occurs by destruction (bleaching) in the exposed areas of the developable silver specks formed by fogging, which can be represented schematically as follows:

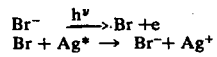

In the interest of sensitivity, recombination of photoelectrons with positive holes (bromide ion that has lost an electron) should be avoided in both systems. Therefore, in the negative system in positive holes should be trapped because the electrons are used in the latent image-formation, whereas in the direct-positive system the electrons should be trapped since the positive holes are responsible for the destruction of the fog nuclei.

In the negative system it is known to incorporate one or more developing agents e.g. polyhydroxybenzenes, aminophenols, and 3-pyrazolidones in the light-sensitive material itself and to effect development after exposure by treatment of the material with alkaline compositions substantially free of developing agents and called activator-solutions. In this way the processing composition can be stored for a very long time, it does not become exhausted so easily and it need not be replenished. The incorporation of developers directly into the silver halide element rather than in the processingsolution also permits the use of simplified processing chemistry and equipment. The developed material can be fixed and washed in the usual way but it is also possible to treat the residual silver halide without removing it in such a way as to stabilize it against the effects of further exposure to actinic light during handling and storage. One method for stabilizing a photographic print is to treat it with an alkali metal thiocyanate or an ammonium thiocyanate and then dry it without-washing. This well known stabilization processing is a rapid-access technique wherein usually surface application of alkaline activator followed by surface application of stabilizer solution are employed to provide a substantially dry, stabilized print in less than 30 seconds. It is possible to obtain archival stability of the prints by including a short fixing and washing step after the stabilizing step as described in U.S. Pat. No. 3,637,389.

It would be worthwhile to extend the advantages of the above processing techniques to the direct-positive system and thus to incorporate the developing agents into the photographic direct-positive material. However, it was found that the incorporation of developing agents into direct-positive silver halide material, though suggested in the prior art, impairs direct-positive image formation and decreases the sensitivity of the system. By the presence of the developing agent in the silver halide emulsion silver halide grains with developable fog centers risk to be developed before exposure. Moreover, due to halogen-accepting (=hole trapping) properties of the silver halide developing agents destruction of the fog centers during exposure is impaired which results in low speeds.

It has not been found that 1,4-dihydroxy benzene compounds wherein at least one of the hydroxyl groups has been esterified to form a hydrolyzable aliphatic acyloxy group comprising a quaternary ammonium substituent are very effective developing agent precursors for use in direct-positive silver halide elements comprising fogged silver halide grains. As compared with the non-chemically masked parent compounds e.g. hydroquinone markedly higher speed values are obtained.

The present invention thus provides a photographic element comprising a support and at least one direct-positive silver halide emulsion layer with fogged silver halide grains wherein the said element comprises in the said emulsion layer and/or in a colloid layer in water-permeable relationship with the said emulsion layer a 1,4-dihydroxybenzene compound of which at least one of the hydroxyl groups has been esterified to form a hydrolyzable aliphatic acyloxy group comprising a quaternary ammonium group.

Such 1,4-dihydroxybenzene developing agent precursor compounds have been described in U.S. Pat. No. 3,650,749 for use in photographic silver halide elements of the negative type, and can be represented more particularly by the following general formula:

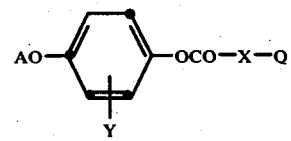

wherein:

Y stands for hydrogen or one or more substituents selected from alkyl such as methyl, ethyl, t-butyl, etc. and halogen such as chlorine, bromine, X stands for methylene or ethylene including methylene or ethylene substituted by alkyl or aryl, Q stands for an ammonium group of one of the formulae:

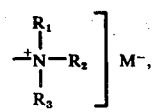

-continued

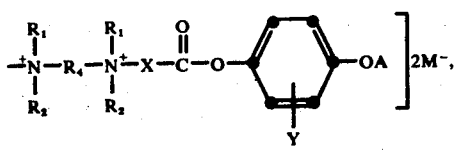

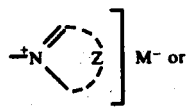

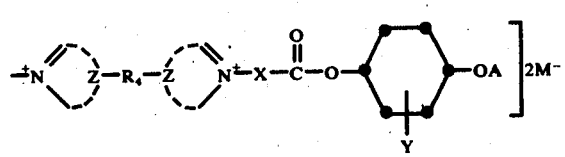

wherein:

M stands for an anion e.g. chlorine or bromine, methyl sulphate, ethyl sulphate, p-toluene sulphonate, etc. but does not exist when one of $R_1$–$R_3$ itself contains an anionic group, each of $R_1$ and $R_2$ stands for an alkyl group preferably a $C_1$–$C_5$ alkyl group or an aralkyl group or together represent the atoms necessary for completing a heterocyclic ring, e.g., morpholine, pyrrolidine and piperidine, $R_3$ stands for an alkyl group or preferably a $C_1$–$C_5$ alkyl group an aralkyl group, $R_4$ stands for an alkylene group, and Z represents the atoms necessary to close a heterocyclic nucleus e.g. pyridine, A stands for hydrogen or the group —COXQ.

Preferred compounds are those wherein Q stands for the group

wherein $R_1$, $R_2$ and $R_3$ have the meanings given above and A stands for hydrogen.

Representative examples of compounds for use according to the present invention are:

1. 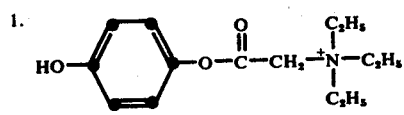 Cl⁻

2. 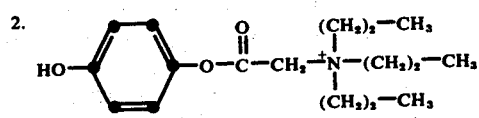 Cl⁻

3. 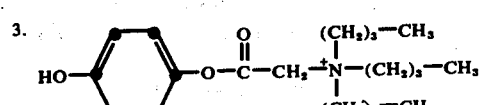 Cl⁻

4. 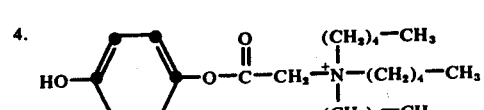 Cl⁻

-continued

5. 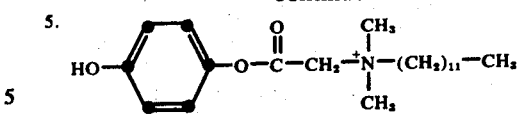 Cl⁻

6. 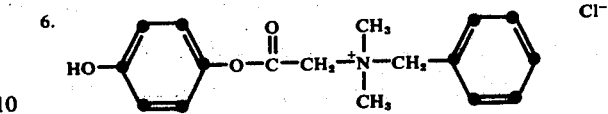 Cl⁻

7. 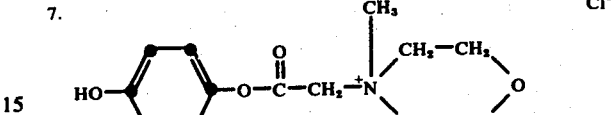 Cl⁻

8. 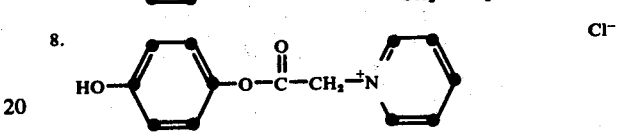 Cl⁻

9. 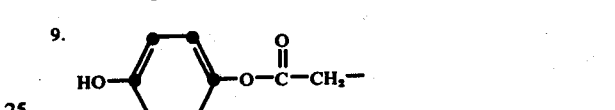

 Cl⁻

10. 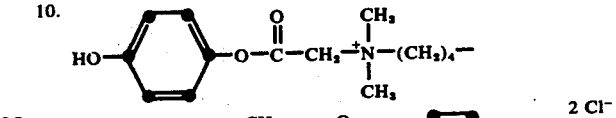

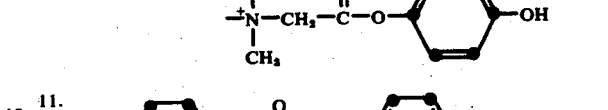 2 Cl⁻

11. 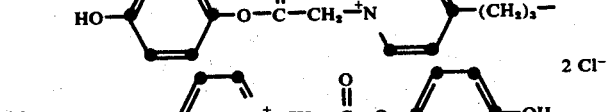

 2 Cl⁻

12. 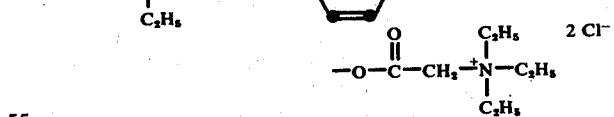

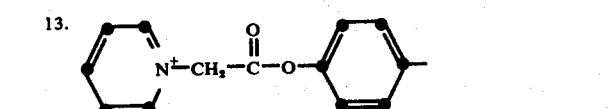 2 Cl⁻

13. 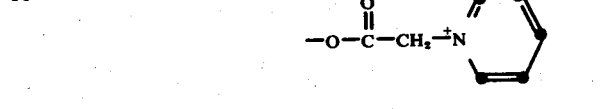

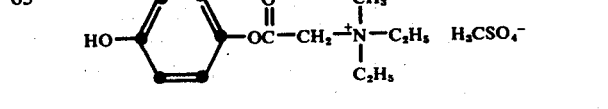 2 Cl⁻

14. 

-continued

15. 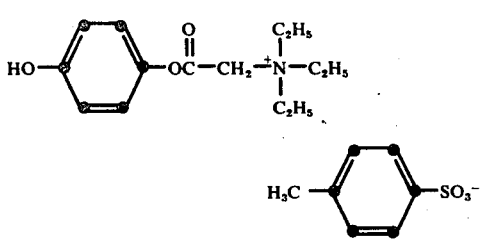

16. 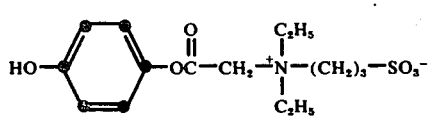

They can be prepared as described in U.S. Pat. No. 3,650,749 by reaction of halogenated esters of the 1,4-dihydroxybenzene with tertiary amines. An alternative method (which is illustrated by the following preparations) comprises reaction of such esters with secondary amines followed by treatment with alkylating agents e.g. the esters of sulphuric acid, phosphoric acid, benzene sulphonic acid, p-toluene sulphonic acid etc. to form the quaternary ammonium group. A further method comprises the reaction of the 1,4-dihydroxybenzene with a quaternary ammonium acetic acid or acetic acid chloride e.g. of the type described in Org. Synth. Coll. Vol. IV (1963) 154–6.

PREPARATION 1 : COMPOUND 14 a. 146 g (2moles) of diethylamine were added dropwise in 15 min. to a solution of 186.5 g (1 mole) of p-chloroacetyloxyphenol in 1 liter of diethyl ether. The mixture was refluxed for 9 hours whereupon the diethylamine hydrochloride was filtered off by suction. The filtrate was concentrated by evaporation and the oil obtained was stirred for three times with 800 ml of benzene. The benzene solution was concentrated by evaporation. Yield: 160 g (71%) of viscous oil.

b. To a solution of 22.3 g (0.1 mole) of p-diethylaminoacetyloxy-phenol in 100 ml of acetone, 12.6 g (0.1 mole) of dimethyl sulphate were added. The mixture was refluxed for 2 hours, poured into diethyl ether and dissolved in ethanol. The product was precipitated in diethyl ether.

Yield: 13 g (37%). Melting point: 132° C.

PREPARATION 2 : COMPOUND 15

A mixture of 22.3 g (0.1 mole) of p-diethylaminoacetyloxyphenol and 20 g (0.1 mole) of ethyl p-toluene sulphonate were heated gradually to 130° C. After three hours the viscous mixture was dissolved in methanol and the solution poured into diethyl ether. The precipitate was recrystallized from acetone.

Yield: 13 g (30%). Melting point: 155° C.

PREPARATION 3 : COMPOUND 16

To a solution of 22.3 g (0.1 mole) of p-diethylaminoacetyloxyphenol in 100 ml of acetone, 12.2 g (0.1 mole) of propane sultone were added. The mixture was refluxed for 5 hours and then poured into ether. The product formed was purified by dissolution in methanol and pouring the methanolic solution with stirring into ethylacetate.

Yield: 11 g (31%). Melting point: about 80° C.

The developer precursor compounds are preferably incorporated in the direct-positive silver halide emulsion comprising fogged silver halide grains. However, it is also possible to use the compounds in a colloid layer in water-permeable relationship with the emulsion layer e.g. an undercoat or overcoat.

The developer precursor compounds of the invention can be incorporated into said silver halide emulsion or other colloid composition by mixing a solution of the precursor compound in a suitable solvent, preferably water, with the said fogged silver halide emulsion or the said colloid composition prior to coating. The solution of the developer precursor may also first be homogeneously admixed with a hydrophilic colloid composition, e.g., aqueous gelatin whereupon the whole is mixed with the photographic emulsion.

The concentration of developer precursor according to the present invention will vary markedly depending upon the particular chemical compound involved, the particular direct positive silver halide emulsion and the location of the compound within the photographic element. When incorporated in the silver halide emulsion layer the amount of development precursor according to the present invention per mole of silver halide is generally such that upon treatment with the activator solution from about 0.01 mole to about 2 moles, preferably from about 0.05 mole to about 1 mole, of hydroquinone can be set free. When incorporated in another colloid layer which is in contact with or which will come into contact with the silver halide emulsion layer on development somewhat larger concentrations can be used.

Since the active developer is set free under alkaline conditions the pH of the emulsion is preferably approximately neutral or acid. The pH of the emulsion to be coated is preferably at most 5. Such low pH values also have a favourable effect on the speed of the direct-positive emulsion as described in United Kingdom Patent Application No. 32889/72.

The photographic direct-positive elements of the invention comprising a developer precursor compound either in a direct-positive silver halide emulsion layer with fogged silver halide grains or in another colloid layer in water-permeable relationship with the emulsion layer can be developed, after exposure, by means of a mere alkaline activator. These activators may be of different compositions. Although a simple solution of an alkaline material e.g. an aqueous solution of sodium hydroxide, potassium hydroxide, sodium carbonate, potassium carbonate, borax, etc. will suffice, it may be advisable to add some other additives e.g. wetting agents, preserving agents such as sodium sulphite and potassium metabisulphite, development accelerators, silver halide solvents, alkali halides e.g. potassium bromide, thickening agents e.g. carboxymethyl cellulose, hardening agents, auxiliary developing agents, etc. Typical auxiliary developing agents include 1-phenyl-3-pyrazolidone and derivatives e.g. 1-p-tolyl-3-pyrazolidinone, 1-phenyl-5-methyl-3-pyrazolidinone, 1-phenyl-4,4-dimethyl-3-pyrazolidinone and 1-acetamidophenyl-3-pyrazolidinone, aminophenol developing agents e.g. p-monomethylaminophenol as well as other auxiliary developing agents known for use together with 1,4-dihydroxybenzene developing agents e.g. hydroquinone. Precursor compounds of these auxiliary developing agents may also be incorporated in the direct-positive photographic elements e.g. 3-pyrazolidone precursor compounds of the type described in U.S. Pat. Nos. 3,241,967 and 3,247,201, Belgian Pat. No. 621,608 and British Pat. No. 943,928.

It is also possible to effect development of the exposed direct-positive elements of the present invention by means of an alkaline activator in the presence of hydroxylamine or a salt thereof or of a N-monsubstituted hydroxylamine or salt thereof as described in the published German Patent Application No. 2,324,161.

The activator solutions may be applied to an exposed direct-positive photographic element according to the present invention in any known way such as by dipping, spraying, surface wetting, etc.

The photographic element developed according to the present invention can be stabilized by conventional fixation and washing or by stabilization. For more details about stabilization processing there can be referred to A. A. Newman "The Chemistry of stabilization processing", The British Journal of Photography, Nov. 1967 p. 1009 and the literature cited therein. Alternatively, the developed material may be treated with a stabilizing and fixing solution as described in U.S. Pat. No. 3,637,389.

The direct-positive photographic elements according to the present invention having incorporated developing agent precursor compounds can be used in the well known silver complex diffusion transfer process to make transfer images either by the one sheet system, in which the emulsion is coated on the same support as the image-receiving layer, or by the two-sheet system, in which the emulsion and image-receiving layer are coated on separate supports. In the silver complex diffusion transfer process the fogged direct-positive emulsion of the invention, upon exposure and treatment with an alkaline solution, forms a direct-positive image of the original (e.g. a negtive when the original is a negative). In the presence of a silver complexing agent, the exposed silver halide which has not developed diffuses into the image-receiving layer where by the action of development nuclei a negative image of the original forms (e.g. a positive image when the original is a negative).

As referred to hereinbefore, it is in the interest of sensitivity to provide electron-traps in fogged direct-positive silver halide emulsions.

Therefore, the direct-positive, fogged silver halide emulsions according to the present invention preferably comprise electron-traps. The direct-positive emulsions may comprise interior electron traps or exterior electron traps. Fogged direct-positive silver halide emulsions with interior electron-traps are emulsions comprising silver halide grains having in their interior centers promoting the deposition of photolytic silver and an outer region of fogged silver halide. Fogged direct-positive silver halide emulsions with exterior electron-traps are emulsions having adsorbed to the surface of the fogged silver halide grains a compound accepting electrons preferably electron-accepting dyes which may provide spectral sensitization or not.

Photographic emulsions comprising in the interior of the silver halide grains centers promoting the deposition of photolytic silver can be prepared, e.g., as described in the United Kingdom patent specification No. 1,027,146 of Agfa A.G. filed Aug. 30, 1963. For this purpose, a fine-grain silver halide emulsion is made first, preferably by the double jet silver halide precipitating technique, and these fine silver halide grains serve as the cores for the final emulsion.

The silver halide cores thus formed are then treated so as to produce centers that promote the deposition of photolytic silver (electron traps) on the cores. For this purpose, the cores may be treated chemically or physically according to any of the known procedures for producing ripening nuclei i.e. latent image nucleating centers. Such procedures are described, e.g., by A. Hautot and H. Sauvenier in "Sci. et Ind. Phot.", Vol. XXVIII, January 1957, p. 1–23 and 57–65.

The ripening nuclei can be formed by chemical sensitization by means of noble metal compounds, especially gold or iridium compounds e.g. the alkaline metal salts of the following noble metal ions $[Au(S_2O_3)_2]^{3-}$, $[Au(SCN)_2]^-$, $[IrX_6]^{3-}$ and $[IrX_6]^{4-}$ wherein X is halogen, by means of sulphur compounds, e.g. thiosulphates, or by means of both noble metal compounds and sulphur compounds. Ripening of the silver halide cores can also be effected by means of reducing agents, e.g. hydrazine, thiourea dioxide or tin(II)chloride, optionally together with noble metal compounds.

Electron traps can further be provided by treating the silver halide cores with aqueous solutions of salts of polyvalent metals e.g. of the trivalent bismuth.

It is also possible to use the compounds suitable for the formation of the electron traps, e.g. the chemical sensitizers to hereinbefore, during the precipitation of the fine-grain silver halide i.e. during the formation of the cores for the final silver halide emulsion. In this way, the electron traps are distributed statistically in the interior of the cores contrary to when the compounds are added after the formation of the fine-grain silver halide where the electron traps are formed substantially at the surface of the cores. After the formation of the cores having centers promoting the deposition of photolytic silver, silver halide precipitation is continued to form around the cores an outer shell of silver halide. The final emulsion is then fogged as described hereinafter.

Direct-positive silver halide emulsions comprising exterior electron traps have adsorbed to the surface of the fogged silver halide grains one or more electron-accepting or desensitizing compounds as described e.g. in the United Kingdom patent specification No. 723,019.

According to Sheppard et al J. Phys. Chem. 50 (1946) 210, Stanienda, Z. Phys. Chem. (NF) 32 (1962) 238, and Dahne, Wiss. Phot. (1969) 161, desensitizers are dyestuffs whose cathodic polarographic half-wave potential, measured against the calomel electrode, is more positive than −1.0 V. Such compounds have also been described in the U.S. Pat. Nos. 3,501,305, 3,501,306, and 3,501,307 all of Bernard D. Illingsworth issued Mar. 17, 1970. The compounds described in the German Patent Specification No. 1,153,246 filed Apr. 11, 1962 by Agfa A.G. and U.S. Pat. No. 3,314,796 of Johannes Gotze, August Randolph and Oskar Riester issued Apr. 18, 1967 are also suitable for this purpose as well as imidazo-quinoxaline dye-stuffs, e.g. those described in the Belgian Patent Specification No. 660,253 filed Feb. 25, 1965 by Kodak Co.

It is known to characterize these electron-accepting or desensitizing compounds by means of their polarographic half-wave potential. Electron acceptors suitable for use in the direct-positive silver halide emulsions of the present invention have an anodic polarographic half-wave potential and a cathodic polargraphic half-wave potential that when added together give a positive sum. Methods of determining these polarographic half-wave potentials have been described, e.g., in the U.S. Pat. Nos. 3,501,310 of Bernard D. Illingsworth issued Mar. 17, 1970 and 3,531,290 of Roberta A. Litzerman issued Sept. 29, 1970.

The electron-accepting compounds preferably have spectrally sensitizing properties although it is possible to use electron-accepting compounds that do not spectrally sensitize the emulsion.

In order to obtain by exposure and development direct-positive silver images without first forming a negative image the silver halide grains of the light-sensitive emulsion must have been surface-fogged which can occur in any suitable known manner previously described in the prior art. The emulsions may be fogged e.g. by an overall exposure to actinic radiation or by reduction sensitization e.g. by high pH and/or low pAg-silver halide precipitating or digestion conditions e.g. as described by Wood, J. Phot. Sci. 1 (1953) 163, or by treatment with reducing agents. Fogging preferably occurs by reduction sensitization in the presence of a compound of a metal more electropositive than silver.

Reducing agents suitable for use include hydrazine, hydroxylamine, tin(II) compounds e.g. tin(II)chloride, tin complexes and tin chelates of the (poly)amino(-poly)carboxylic acid type as described in British patent specification No. 1,209,050, ascorbic acid, formaldehyde, thiourea dioxide, polyamines such as diethylene triamine, phosphonium salts such as tetra(hydroxymethyl)phosphonium chloride, bis(p-aminoethyl) sulphide and its water-soluble salts, etc. Preferred reducing agents are thiourea dioxide and tin(II)chloride.

The compounds of a metal more electropositive than silver include gold compounds e.g. potassium tetrachloroaurate, auric trichloride, and potassium aurithiocyanate, as well as compounds of rhodium, ruthenium, platinum, iridium, and palladium e.g. ammonium hexachloropalladate and potassium chloroiridate. Preferred noble metal compounds are gold compounds.

When fogging of the silver halide grains occurs by means of a reducing agent e.g. thiourea dioxide and a compound of a metal more electropositive than silver especially a gold compound, the reducing agent is preferably used initially and the gold compound subsequently. However, the reverse order can be used or both compounds can be used simultaneously.

The degree of fogging of the direct-positive silver halide emulsions may vary within a wide range. As is known in the art the degree of fogging not only depends on the concentration of the fogging agents used but also on the pH, the pAg, the temperature and the duration of the fogging treatment. Fogging of the silver halide grains is preferably effected at neutral or higher pH-values e.g. a pH-value of at least 6.5 and at a pAg-value below 8.35, preferably below 7.7.

High photographic sensitivities are obtained at low degrees of fogging as is illustrated in U.S. Pat. No. 3,501,307 and British patent application No. 7742/72. Thus, the degree of fogging can be adapted according to the requirements of desired sensitivity and the terms fogged and fogging as used herein are therefore employed in a very broad sense so that the very low degrees of fogging as defined in U.S. Pat. No. 3,501,307 and British patent application No. 7742/72 are also embraced. This means that fogging is effected to such extent that a test portion of the fogged emulsions when coated on a support at a coverage of 0.50 to 5.50 g of silver per sq.m, gives a density of at least 0.50 upon processing for 3 min at 20° C in a developer of the following composition:

| | |
|---|---|
| hydroquinone | 15 g |
| 1-phenyl-3-pyrazolidinone | 1 g |
| trisodium salt of EDTA | 1 g |
| anhydrous sodium carbonate | 30 g |
| anhydrous sodium sulphite | 70 g |
| 40 % aqueous sodium hydroxide | 16 ml |
| water to make | 1 liter |
| (pH : 11) | |

The silver halides of the direct-positive silver halide emulsions of the present invention may be silver chloride, silver bromide, or silver chlorobromide, which all may comprise up to 20 mole % of silver iodide. In the silver halide emulsions comprising interior electron-traps the silver halides of the core and of the shell may be the same or different e.g. the core may be silver chloride and the shell silver chloride, or silver bromide, silver chlorobromide, silver chlorobromoiodide, or silver bromoiodide.

In the direct-positive emulsions of the invention, the grains may also be provided with a thin protective envelope to improve the fog stability as described in the published German Patent Application No. 2,216,075.

Especially suitable for use in accordance with the present invention are direct-positive silver halide emulsions the silver halide grains of which have an averge grain diameter of less than about 1 micron, preferably less than 0.5 micron. The silver halide grains may be regular and may have any of the known shapes e.g. octahedral, rhombohedral and preferably cubic. They may have a substantially uniform diameter frequency distribution e.g. 95% by weight of the silver halide grains can have a diameter which is within about 40%, preferably within about 30% of the means grain diameter.

In the preparation of the direct-positive photographic silver halide emulsion for use in accordance with the present invention gelatin is preferably used as vehicle for the silver halide grains. However, the gelatin may be wholly or partly replaced by other natural hydrophilic colloids, e.g. albumin, zein, agar-agar, gum arabic, alginic acid, and derivatives thereof e.g. salts, amides and esters, starch and derivatives thereof, cellulose derivatives e.g. cellulose ethers, partially hydrolyzed cellulose acetate carboxymethyl cellulose, etc. or synthetic hydrophilic resins, for example polyvinyl alcohol, polyvinyl pyrrolidone, homo- and copolymers of acrylic and methacrylic acid or derivatives e.g. esters, amides and nitriles, vinyl polymers e.g. vinyl ethers and vinyl esters.

The direct-positive silver halide emulsions for use in accordance with the present invention may comprise additional additives known to be beneficial in photographic emulsions. They may comprise e.g. speed-increasing compounds, stabilizers, antistatic agents, coating aids, optical brightening agents, light-absorbing dyes, plasticizers and the like.

Spectrally sensitizing dyes that are not electron-accepting such as e.g. cyanines, merocyanines, complex (trinuclear) cyanines, complex (trinuclear) merocyanines, styryls, and hemicyanines may also be present in the emulsion.

The direct-positive emulsions containing in their interior centres promoting the deposition of photolytic silver may also contain compounds increasing the blue sensitivity, e.g. as described in United Kingdom Patent Specification 1,186,718. Compounds of this type have an anodic polarographic potential of less than 0.85 and a cathodic plarographic potential with a value that is more negative than −1.0. Suitable blue speed increasing compounds have also been described e.g. in the U.S. Pat. No. 3,531,290.

The silver halide emulsion layer and other hydrophilic colloid layers of a direct-positive photographic material employed in accordance with the present invention may be hardened by means of organic or inorganic hardeners commonly employed in photographic silver halide elements, e.g. the aldehydes and blocked aldehydes such as formaldehyde, dialdehydes, hydroxyaldehydes, mucochloric and mucobromic acid, acrolein, glyoxal, sulphonyl halides and vinyl sulphones, etc.

The direct-position silver halide emulsions can be coated on one or both sides of a wide variety of supports, which include opaque supports e.g. paper and metal supports as well as transparent supports e.g. glass, cellulose nitrate film, cellulose ester film, polyvinyl acetal film, polystyrene film, polyethylene terephthalate film, polycarbonate film and other films of resinous materials. It is also possible to use paper coated with α-olefin polymers e.g. paper coated with polyethylene, polypropylene, ethylenebutene copolymers etc.

Before coating of the direct-positive silver halide emulsion and preferably after addition of the electron-accepting compounds or of the blue speed increasing compounds and of the possible spectrally sensitizing dyes, the pAg of the emulsion may be increased e.g. by addition of potassium bromide and/or potassium iodide, in order to enhance the speed and stability of the direct-positive silver halide emulsions. Favourable photographic speeds are obtained when the pAg is adjusted, before coating, to a valve of about 9 or higher.

Photographic materials, which contain at least one of the direct-positive silver salt emulsion layers according to the invention may be used for various photographic purposes, e.g. as materials with a steep gradation for reprographic purposes, as direct-positive X-ray films, in the silver complex diffusion transfer process, etc.

EXAMPLE 1

A mono-disperse, cubic, direct-positive photographic emulsion containing approximately 80 mole % silver chloride, 18 mole % silver bromide and 2 mole % silver iodide, and having an average grain size of 0.25 micron, was prepared under controlled pH, pAg and temperatue conditions during the precipitation of the mixed silver halide. The pH was maintained at 5, the pAg at 6.83 and the temperature at 60° C. The emulsion was chill-set, shredded and washed with cold water. At 40° C, gelatin and water were added in order to obtain a gelatin to silver nitrate ratio of 0.6 and a concentration of silver halide corresponding to 160 g of silver nitrate pro kg of emulsion. The emulsion was digested at 57° C, pH 7 and pAg 6.16 for about 2 h in the presence of potassium chloroaurate (1.5 mg/mole of silver nitrate).

After addition of 500 mg of pinacryptol yellow and 340 mg of the following spectral sensitizer:

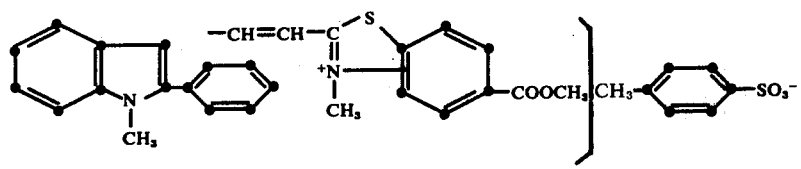

per mole of silver halide, the pH and pAg of the emulsion were adjusted with sulfuric acid and potassium bromide to pH 5 and pAg 9.60.

The emulsion was divided into several aliquot portions and to each portion hydroquinone or a hydroquinone precursor compound as listed in the table hereinafter were added in an amount of 0.2 mole per mole of silver halide.

The emulsion portions were coated on a support, exposed in a sensitometer and developed for 90 seconds at 20° C in a solution of the following composition:

| | |
|---|---|
| sodium hydroxide | 30 g |
| sodium sulphite | 50 g |
| potassium bromide | 2 g |
| water to make 1 liter | |

For one experiment 1-phenyl-3-pyrazolidinone was added to this solution in an amount of 1 g per liter.

The sensitometric results obtained are listed in the following table. The values given for the speed are relative values for the speed measured at $\frac{D_{max} - D_{min}}{2}$ A value of 100 was given to the speed of the emulsion comprising hydroquinone.

Table

| Developing agent in the emulsion | $D_{min}$ | $D_{max}$ | Relative speed |
|---|---|---|---|
| hydroquinone | 0.08 | 3.34 | 100 |
| mono-chloroacetic acid ester of hydroquinone | 0.08 | 1.12 | 12 |
| compound 7 | 0.10 | 1.91 | 1630 |
| compound 6 | 0.10 | 1.97 | 1630 |
| compound 3 | 0.10 | 2.13 | 1780 |
| compound 2 | 0.10 | 1.91 | 1740 |
| compound 1 | 0.10 | 2.54 | 1700 |
| compound 1 | 0.12 | >4.00 | 1350 |
| (and 1 g of 1-phenyl-3-pyrazolidinone in developing solution0 | | | |
| compound 10 | 0.10 | 1.91 | 263 |
| compound 12 | 0.08 | 2.12 | 151 |
| compound 12 (and 1 g of 1-phenyl-3-pyrazolidinone in developing solution) | 0.08 | 3.40 | 126 |

The above results show that higher speeds are obtained with the developing agent precursors of the invention than with hydroquinone or the mono-chloroacetic acid ester of hydroquinone which is also a hydroquinone developing agent precursor.

EXAMPLE 2

Portions of the emulsion described in example 1 were coated on a support which was provided previously with a gelatin layer containing one of the developing agents listed in the table below in the amount given. The emulsions were coated so that per sq.m an amount of silver halide equivalent to 5 g of silver nitrate was present.

The materials were exposed in a sensitometer and developed for 20 sec at 30° C in a solution of the following composition:

| | |
|---|---|
| sodium carbonate | 100 g |
| sodium hydroxide | 10 g |
| (NH$_2$OH)$_2$ . H$_2$SO$_4$ | 5 g |
| sodium sulphite | 5 g |
| potassium bromide | 3 g |
| water to make | 1 liter |

The sensitometric results obtained are listed in the following table. The values given for the speed are relative values for the speed measured at $\frac{D_{max} - D_{min}}{2}$

Table

| developing agent per sq.m | $D_{min}$ | $D_{max}$ | Relative speed |
|---|---|---|---|
| none | 0.04 | 0.05 | — |
| 3.58 mmole of hydroquinone | 0.85 | 2.58 | 100 |
| 1.15 mmole of compound 6 | 0.06 | 1.25 | 254 |
| 0.86 mmole of compound 12 | 0.07 | 1.60 | 251 |

The above results clearly illustrate the superiority of the hydroquinone precursor compounds over hydroquinone.

We claim:

1. A direct-positive photographic element comprising a support and at least one direct-positive silver halide emulsion layer containing fogged silver halide grains wherein the said element comprises in the emulsion layer and/or in a colloid layer in water-permeable relationship with the emulsion layer a 1,4-dihydroxybenzene compound wherein at least one of the hydroxyl groups has been esterified to form a hydrolyzable aliphatic acyloxy group comprising a quaternary ammonium group having the general formula:

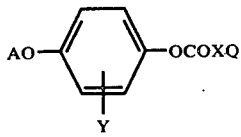

wherein:
Y is hydrogen, alkyl or halogen,
X is methylene or ethylene which may be substituted by alkyl or aryl,
Q is an ammonium group of the formula:

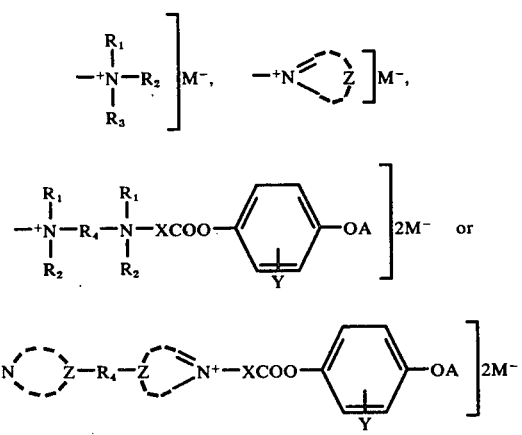

wherein:
M is an anion,
each of R$_1$ and R$^2$ is alkyl or aralkyl or together represent the atoms necessary to complete a heterocyclic ring selected from the group consisting of morpholine, pyrrolidine, and piperidine,
R$_3$ is alkyl or aralkyl,
R$_4$ is an alkylene group, and
Z represents the atoms necessary to close a heterocyclic nucleus,
A stands for hydrogen or the group —CO-X-Q.

2. A direct-positive photographic element according to claim 1 wherein A is hydrogen.

3. A direct-positive photographic element according to claim 1, wherein the fogged silver halide grains are obtained by reduction sensitization of the silver halide emulsion in the presence of a compound of a metal more electropositive than silver.

4. A direct-positive photographic element according to claim 3, wherein the compound of a metal more electro-positive than silver is a gold compound.

5. A direct-positive photographic element according to claim 3 wherein reduction sensitization occurs by high pH and/or low pAg halide digestion conditions.

6. A direct-positive photographic element according to claim 1 wherein Q is

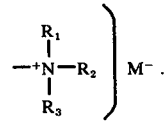

7. A direct-positive photographic element according to claim 1 wherein the pH of the silver halide emulsion layer and/or colloid layer is below 7.

8. A direct-positive photographic element according to claim 1 wherein the pH of the silver halide emulsion layer and/or colloid layer is 5 or below.

* * * * *